US00PP21077P3

(12) United States Plant Patent
Tully

(10) Patent No.: US PP21,077 P3
(45) Date of Patent: Jun. 22, 2010

(54) ***HEBE* PLANT NAMED 'TULLYRASPB'**

(50) Latin Name: *Hebe×hybrida*
Varietal Denomination: TULLYRASPB

(76) Inventor: Martin Tully, Tully Nurseries Limited Richardstown, Ballyboughal, County Dublin (IE)

( * ) Notice: Subject to any disclaimer, the term of this patent is extended or adjusted under 35 U.S.C. 154(b) by 0 days.

(21) Appl. No.: 12/321,536

(22) Filed: Jan. 20, 2009

(65) Prior Publication Data

US 2009/0193557 P1 Jul. 30, 2009

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para

(57) ABSTRACT

A new cultivar of *Hebe* plant named 'TULLYRASP' that is characterized by a compact habit with deep burgundy colored foliage and which bears abundant deep pink flowers through summer and fall. In combination these traits set 'TULLYRASP' apart from all other varieties of *Hebe* known to the inventor.

3 Drawing Sheets

Genus: *HEBE*.
Species: ×*hybrida*.
Denomination: 'TULLYRASPB'.

BACKGROUND OF THE INVENTION

This application claims the benefit of priority under 35 U.S.C. 119(f) of the application for a grant of European Community Plant Breeders Rights which was filed for the instant plant variety on Jan. 25, 2008, Application Number 2008/0177.

The present invention relates to a new and distinct cultivar of *Hebe* that is grown for use as a flowering plant for use in containers and in the garden and landscape. The new cultivar is known botanically as *HEBE×hybrida* and will be referred to hereinafter by the cultivar name 'TULLYRASPB'.

'TULLYRASPB' is the product of a breeding program started by the inventor in 1998. The breeding program is ongoing, and is conducted at the inventor's nursery in Ballyboughal, County Dublin, Republic of Ireland. The primary focus of the breeding program is to produce new cultivars of *Hebe* which are extremely compact and which possess colorful foliage and abundant flowers. These characteristics in combination are considered by the inventor to be of most interest to the relevant market.

The breeding of 'TULLYRASPB' proceeded as follows: First, the inventor assembled several potential parent varieties, including the commercially available cultivars 'Autumn Glory' (not patented), 'Marjorie' (not patented), 'Margret' (U.S. Plant Pat. No. 8,231), 'Oratio Beauty' (not patented), 'Red Edge' (not patented), 'Albicans' (not patented), 'Mrs. Winder' (not patented), 'Black Beauty' (not patented), 'Great Orme' (not patented), 'Pink Wand' (not patented) together with un-named and un-released varieties of the inventor's own development. Specimen plants of each of these varieties were placed in close proximity at the inventor's nursery in order to facilitate natural pollination. Pollination was not controlled and occurred naturally by means of insects and wind. The parentage was not restricted or monitored and may even have involved varieties not listed herein that were outside of the breeding area as a result of insects carrying pollen in. Once mature, seed was collected from these plants without segregation by parent plant. All of the collected seeds were sown and the new variety, 'TULLYRASPB' was selected in the spring of 2004 from amongst the resultant seedlings.

'TULLYRASPB' was selected by the inventor for its combination of compact habit, burgundy colored foliage and deep pink flowers. The variety of *Hebe* which the inventor considers most closely resembles 'TULLYRASP' is one of the possible parent varieties, 'Mrs. Winder'. In comparison with 'Mrs. Winder', 'TULLYRASPB' is more compact, has deeper burgundy foliage and deeper pink flowers.

Asexual reproduction of the new cultivar was first accomplished by the inventor at the inventor's nursery in 2004. The method of asexual propagation used was softwood cuttings. The inventor has determined that 'TULLYRASP' stable and reproduces true to type in successive generations of asexual propagation.

SUMMARY OF THE INVENTION

The following traits have been repeatedly observed and represent the characteristics of the new *HEBE* cultivar 'TULLYRASPB'. These traits in combination distinguish this cultivar from all other commercial varieties known to the inventor. 'TULLYRASPB' has not been tested under all possible conditions and phenotypic differences may be observed with variations in environmental, climatic and cultural conditions, however, without any variance in genotype.

1. *HEBE* 'TULLYRASPB' exhibits a compact habit.
2. *HEBE* 'TULLYRASPB' blooms profusely.
3. The flowers of *HEBE* 'TULLYRASPB' are deep pink in color and are borne through summer and fall.
4. *HEBE* 'TULLYRASPB' exhibits deep burgundy colored foliage.
5. After 15 months of growth, 'TULLYRASP' achieves a height of 15 cm and a width of 15 cm.
6. At maturity in the landscape, 'TULLYRASPB' is 45 cm in height and 45 cm in width.
7. *HEBE* 'TULLYRASPB' is hardy to −5° C.

BRIEF DESCRIPTION OF THE DRAWINGS

The accompanying color drawings illustrate the overall appearance of the new *HEBE* variety 'TULLYRASPB' showing colors as true as it is reasonably possible to obtain in colored reproductions of this type. Colors in the drawings may differ from the color values cited in the detailed botanical description, which accurately describe the actual colors of the new variety 'TULLYRASPB'.

The drawing labeled as FIG. 1 depicts an entire flowering plant of 'TULLYRASP'.

Figure 1:
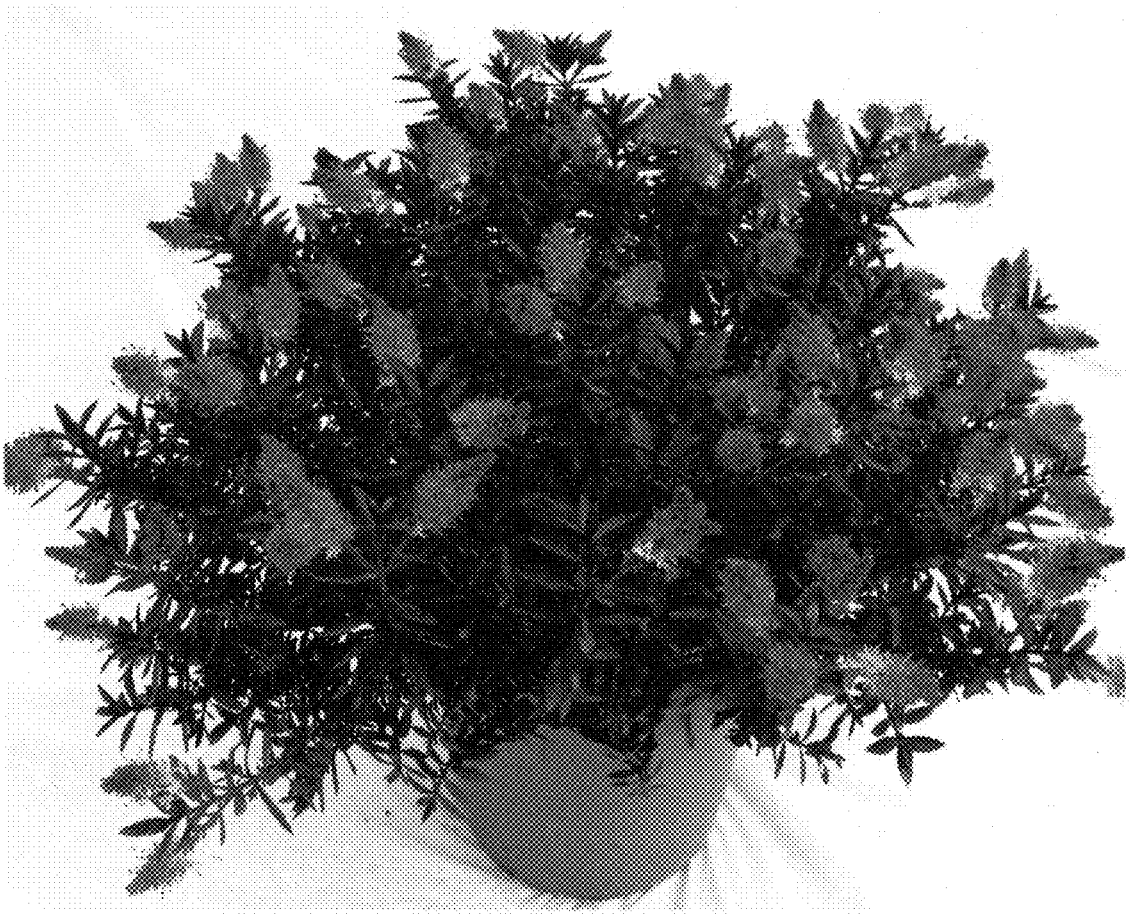
Figure 2:
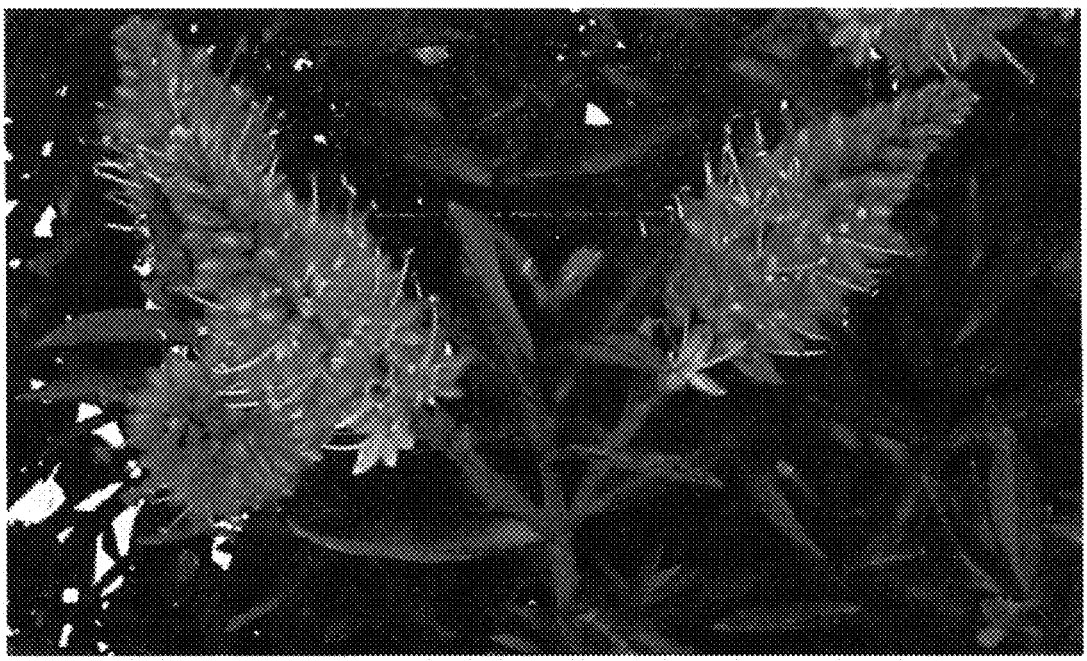

The drawing labeled as FIG. 2 depicts a close-up view of an inflorescence of 'TULLYRASPB' at the point of maximum pink coloration. The individual flowers nearest the apex of the inflorescence are in pink bud and the oldest flowers at the base are just beginning to senesce.

Figure 3:
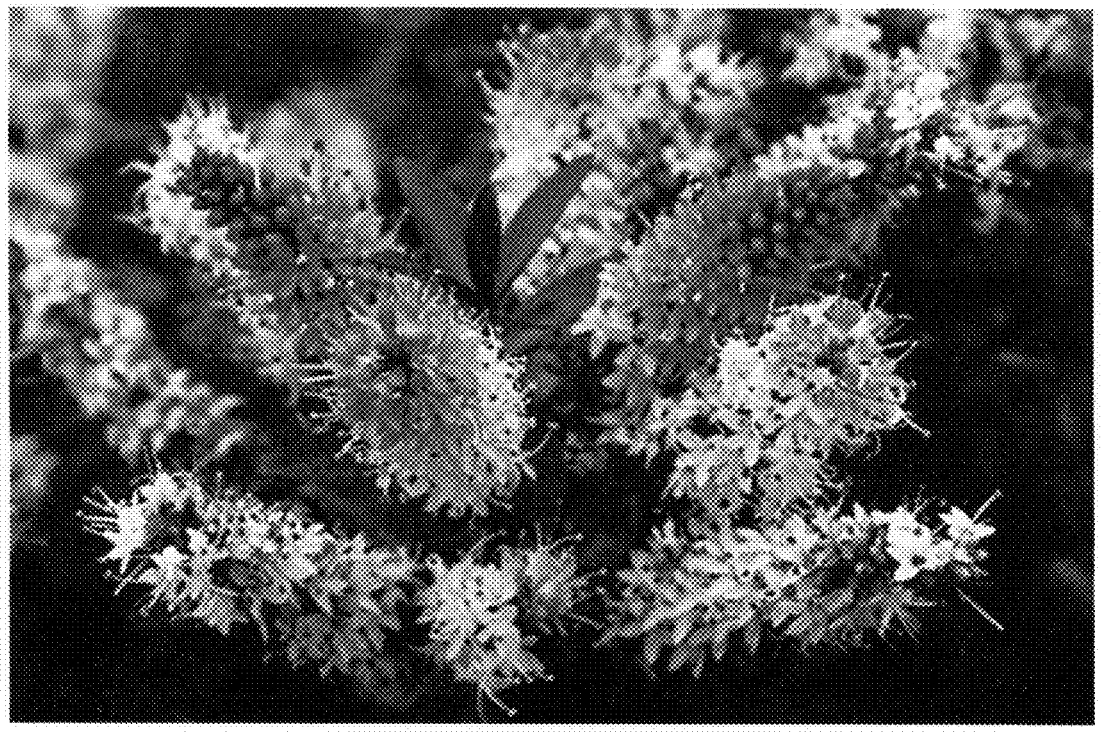

The drawing labeled as FIG. 3 depicts a close-up view of an inflorescence of 'TULLYRASPB' as the flowers senesce and turn first to white and then to brown. The inflorescence shown in this drawing FIG. 3 is approximately two weeks older than the inflorescence shown in FIG. 2.

All drawings were made of 18 months old plants grown in 1 liter containers out of doors at the inventor's nursery in Ballyboughal, County Dublin, Republic of Ireland. No chemicals were used to treat the plants. All drawings were made using conventional techniques and although colors may appear different from actual colors due to light reflectance they are as accurate as possible by conventional photography.

DETAILED BOTANICAL DESCRIPTION

The following is a detailed description of the new cultivar 'TULLYRASPB'. Data was collected in spring from 15 months old plants grown in 1 liter containers out of doors at the inventor's nursery in Ballyboughal, County Dublin, Republic of Ireland. The color determinations are in accordance with the 2007 edition of The Royal Horticultural Society Colour Chart, except where general color terms of ordinary dictionary significance are used.

Botanical classification:

Genus: *HEBE*.

Species: ×*hybrida*.

Denomination: 'TULLYRASP'.

Use: Flowering plant for use in containers and in the garden and landscape.

Parentage: Unknown: 'TULLYRASPB' is a hybrid plant that resulted from uncontrolled open pollination.

Plant description:

*Bloom period.*—June to September.

*Plant habit.*—Compact, upright habit.

*Branching habit.*—Freely branching from lower stem. Apical branches ascending unbranched until branching occurs at 23 cm from apex.

*Vigor.*—Slow-growing.

*Plant dimensions at* 15–18 *months.*—Width: 15 cm. Height: 15 cm.

*Plant dimensions* (*at maturity in the landscape*).—Width: 45 cm Height: 45 cm.

*Hardiness.*—Hardy to minus 5° Centigrade.

*Root system.*—Fibrous.

*Propagation.*—Propagation is accomplished using softwood cuttings.

*Time to develop roots.*—4 weeks at 16–18° Centigrade air temperature.

*Crop time.*—A minimum of 14 months is needed to produce a finished plant in flower in a 1 liter container.

*Recommended growing conditions.*—Free draining soil and planting in full sun or half shade.

*Disease and pest problems.*—Plant is susceptible to root rot in any poor-draining soil and to downy mildew in conditions of high humidity and poor air circulation.

Stem:

*Stem shape.*—Cylindrical.

*Stem dimensions.*—Length 13 cm. Diameter 0.3 cm.

*Stem color* (*new growth*).—152A.

*Stem color* (*mature stem*).—200A.

*Stem surface.*—Smooth.

*Internode distance.*—0.5 cm.

Foliage:

*Type.*—Evergreen, remains unchanged in appearance year-round.

*Arrangement.*—Opposite.

*Shape.*—Elliptic.

*Curvature.*—Young leaves concave, older leaves flat.

*Margins.*—Entire.

*Apex.*—Sub-acute.

*Base.*—Truncate.

*Venation pattern.*—Absent, except for midrib.

*Midrib* (*upper surface*).—Depressed, slight groove.

*Midrib* (*lower surface*).—Thickened (slightly protruding).

*Midrib color:* (*adaxial surface*).—187B, but less prominent or not visible at all in older leaves.

*Midrib color:* (*abaxial surface*).—N186C on young leaves, matches abaxial leaf surface on older leaves.

*Leaf length.*—3.6 cm.

*Leaf width.*—1.2 cm.

*Texture.*—Leathery.

*Attachment.*—Sessile, slightly decurrent.

*Leaf aspect.*—Generally slightly erect, tending to semi-erect towards apex.

*Leaf bud shape.*—Terete.

*Leaf surfaces* (*adaxial and abaxial*).—Smooth.

*Leaf margins.*—Slightly thickened, rounded edge, smooth, entire. N186C.

*Leaf color* (*abaxial surface*).—Young leaf: N186C, mature leaf: 146A.

*Leaf color* (*adaxial surface*).—Young leaf: 187B, mature leaf: 147A.

*Fragrance.*—Absent.

Flowers:

*Inflorescence form.*—Raceme.

*Flower arrangement.*—Flowers are arranged in whorls, as is typical of the species and its known cultivars.

*Inflorescence shape.*—Conical, length 6 cm, diameter (at base) 3 cm.

*Flower development.*—In clusters, commencing at base of raceme.

*Bud shape.*—Elliptic cone.

*Bud color.*—61B.

*Bud surface.*—Smooth.

*Bud dimensions: Length:* 3 mm. Diameter: 1.0 mm–1.5 mm.

*Shape of corolla tube.*—Cylindrical.

*Corolla tube dimensions: Length:* 5 mm. Diameter: 1.5 mm.

*Surface of corolla tube.*—Smooth.

*Corolla tube color.*—NN155D.

*Flower dimensions* (*calyx, corolla tube, and lobes*).—Length: 7 mm. Diameter: 9 mm–11 mm.
*Number of corolla lobes.*—Four.
*Number of petals.*—Four.
*Petal dimensions* (*excluding corolla*).—Length: 5 mm. Width: 2 mm.
*Petal apex shape.*—Acuminate.
*Color of petals.*—Newly open 61B except basal one-third NN155D; entire petal ages to NN155D.
*Petals fused or unfused.*—Petals are basally fused.
*Shape of petals.*—Spatulate.
*Flower aspect.*—Facing outward.
*Quantity of flowers per whorl.*—60.
*Fragrance.*—Not observed.
*Peduncle dimensions.*—Diameter: 1 mm–2 mm. Length: 3 cm–8 cm.
*Peduncle shape.*—Cylindrical.
*Peduncle surface.*—Smooth.
*Peduncle color.*—137C.
*Pedicel dimensions.*—Length: 2 mm–3 mm. Diameter: 0.5 mm.
*Pedicel shape.*—Cylindrical.
*Pedicel surface.*—Smooth.
*Pedicel color.*—137C.
*Calyx shape.*—Cylindrical.
*Number of sepals.*—Four, 2.5 mm in length, 1 mm in width.
*Fused or unfused.*—Basally fused.
*Sepal color.*—137C.
*Sepal apex.*—Acuminate.
*Sepal base.*—Cuneate.
*Sepal surface.*—Lightly pubescent.

Reproductive organs:
*Stigma shape.*—Narrowly capitate.
*Stigma dimensions.*—Approximately 0.2 mm. in width.
*Stigma color.*—Yellow.
*Style shape.*—Filiform.
*Style dimensions.*—Length: 6 mm. Diameter: <0.5 mm.
*Style color.*—White.
*Stamens.*—Two in number, slightly diverging, fused at the base, creating a V-shape.
*Dimensions of stamens.*—10 mm in length, <0.5 mm in width. Stamens are exserted by approximately 7 mm.
*Color of filament.*—White.
*Anther shape and dimensions.*—Capitate, 1 mm in length and width.
*Anther color.*—N77A.
*Pollen amount.*—Slight.
*Pollen color.*—NN155C.
*Ovary shape and position.*—Ovoid, Inferior.
*Ovary dimensions.*—Approximately 1 mm long and 0.75 mm in width.

Seed: No seed has been observed.

The invention claimed is:

1. A new and distinct cultivar of *Hebe* plant named 'TULLYRASPB' as described and illustrated herein.

* * * * *